United States Patent
Levesque (10) Patent No.: US 9,202,352 B2
(45) Date of Patent: Dec. 1, 2015

(54) AUTOMATIC HAPTIC EFFECT ADJUSTMENT SYSTEM

(71) Applicant: Immersion Corporation, San Jose, CA (US)

(72) Inventor: Vincent Levesque, Montreal (CA)

(73) Assignee: Immersion Corporation, San Jose, CA (US)

( * ) Notice: Subject to any disclaimer, the term of this patent is extended or adjusted under 35 U.S.C. 154(b) by 247 days.

(21) Appl. No.: 13/792,754

(22) Filed: Mar. 11, 2013

(65) Prior Publication Data

US 2014/0253303 A1 Sep. 11, 2014

(51) Int. Cl.
| | |
|---|---|
| H04B 3/36 | (2006.01) |
| G08B 6/00 | (2006.01) |
| A61B 5/00 | (2006.01) |
| G06F 3/01 | (2006.01) |

(52) U.S. Cl.
CPC ............... *G08B 6/00* (2013.01); *A61B 5/0002* (2013.01); *G06F 3/011* (2013.01); *G06F 3/016* (2013.01); *G06F 2203/011* (2013.01)

(58) Field of Classification Search
CPC .......... G08B 6/00; G08B 21/22; G06F 3/016; G06F 19/3418; G06F 19/3406; A61B 5/0002; A61B 5/0482
USPC ................ 340/573.1, 407.2, 439, 669, 407.1; 600/558, 300, 301, 545, 544, 28, 595, 600/345, 27
See application file for complete search history.

(56) References Cited

U.S. PATENT DOCUMENTS

| | | | | |
|---|---|---|---|---|
| 8,655,437 | B2 * | 2/2014 | Pradeep et al. | 600/544 |
| 2002/0198717 | A1 * | 12/2002 | Oudeyer et al. | 704/270 |
| 2007/0063849 | A1 * | 3/2007 | Rosella et al. | 340/573.1 |
| 2007/0066916 | A1 * | 3/2007 | Lemos | 600/558 |
| 2007/0265507 | A1 * | 11/2007 | de Lemos | 600/300 |
| 2008/0319279 | A1 * | 12/2008 | Ramsay et al. | 600/301 |
| 2009/0088659 | A1 * | 4/2009 | Graham et al. | 600/545 |
| 2009/0164549 | A1 * | 6/2009 | Jung et al. | 709/201 |
| 2009/0167677 | A1 * | 7/2009 | Kruse et al. | 345/156 |
| 2009/0327068 | A1 * | 12/2009 | Pradeep et al. | 705/14.43 |
| 2010/0013653 | A1 * | 1/2010 | Birnbaum et al. | 340/669 |
| 2010/0123588 | A1 * | 5/2010 | Cruz Hernandez | 340/573.1 |
| 2010/0152545 | A1 * | 6/2010 | Ramsay et al. | 600/301 |
| 2010/0152620 | A1 * | 6/2010 | Ramsay et al. | 600/595 |
| 2011/0009193 | A1 * | 1/2011 | Bond et al. | 463/36 |
| 2011/0050404 | A1 * | 3/2011 | Nakamura et al. | 340/407.1 |
| 2011/0300847 | A1 * | 12/2011 | Quy | 455/419 |
| 2012/0056733 | A1 * | 3/2012 | Ramsay et al. | 340/407.2 |

(Continued)

OTHER PUBLICATIONS

David Birnbaum et al., U.S. Appl. No. 13/597,300, filed Aug. 29, 2012.

(Continued)

*Primary Examiner* — Hoi Lau
(74) *Attorney, Agent, or Firm* — Miles & Stockbridge, P.C.

(57) ABSTRACT

A system is provided that automatically adjusts a haptic effect. The system generates a haptic effect based on one or more haptic parameters. The system measures an affective state of a user that experiences the haptic effect. The system adjusts at least one haptic parameter of the one or more haptic parameters based on the measured affective state. The system generates a new haptic effect based on the one or more haptic parameters, where the at least one haptic effect parameter causes the new haptic effect to be different from the haptic effect.

22 Claims, 7 Drawing Sheets

(56) References Cited

U.S. PATENT DOCUMENTS

| | | | | |
|---|---|---|---|---|
| 2012/0116672 A1* | 5/2012 | Forutanpour et al. | | 701/431 |
| 2012/0123232 A1* | 5/2012 | Najarian et al. | | 600/345 |
| 2012/0124122 A1* | 5/2012 | el Kaliouby et al. | | 709/202 |
| 2012/0131455 A1* | 5/2012 | Han et al. | | 715/702 |
| 2012/0251989 A1* | 10/2012 | Wetmore et al. | | 434/236 |
| 2013/0063256 A1* | 3/2013 | Tartz et al. | | 340/407.1 |
| 2013/0100008 A1* | 4/2013 | Marti et al. | | 345/156 |
| 2013/0103624 A1* | 4/2013 | Thieberger | | 706/12 |
| 2013/0123570 A1* | 5/2013 | Ly et al. | | 600/27 |
| 2013/0190556 A1* | 7/2013 | Wetmore et al. | | 600/28 |
| 2014/0062682 A1* | 3/2014 | Birnbaum et al. | | 340/407.2 |
| 2014/0125474 A1* | 5/2014 | Gunaratne | | 340/439 |
| 2014/0232534 A1* | 8/2014 | Birnbaum et al. | | 340/407.1 |
| 2014/0253303 A1* | 9/2014 | Levesque | | 340/407.1 |
| 2014/0257536 A1* | 9/2014 | Lacroix et al. | | 700/91 |

OTHER PUBLICATIONS

David Birnbaum et al., U.S. Appl. No. 13/593,626, filed Aug. 24, 2012.

Regan L. Mandryk et al., "A Continuous and Objective Evaluation of Emotional Experience with Interactive Play Environments", CHI 2006 Proceedings, Novel Methods: Emotions, Gestures, Events, Apr. 22-27, 2006, XP040037604.

* cited by examiner

AUTOMATIC HAPTIC EFFECT ADJUSTMENT SYSTEM

FIELD

One embodiment is directed generally to haptic effects, and more particularly, to a device that generates haptic effects.

BACKGROUND

Haptics is a tactile and force feedback technology that takes advantage of a user's sense of touch by applying haptic feedback effects (i.e., "haptic effects"), such as forces, vibrations, and motions, to the user. Devices, such as mobile devices, touchscreen devices, and personal computers, can be configured to generate haptic effects. In general, calls to embedded hardware capable of generating haptic effects (such as actuators) can be programmed within an operating system ("OS") of the device. These calls specify which haptic effect to play. For example, when a user interacts with the device using, for example, a button, touchscreen, lever, joystick, wheel, or some other control, the OS of the device can send a play command through control circuitry to the embedded hardware. The embedded hardware then produces the appropriate haptic effect.

Haptic effects are often designed with the intent to produce a specific affective state in users, where an affective state is a representation of an emotive state, such as happy, sad, annoyed, or angry. For example, a haptic effect that acts as an alert may be designed to attract attention to an event without causing annoyance. Similarly, a haptic effect could be designed to produce a pleasant or unpleasant sensation, depending on the context. Designing such haptic effects typically requires manually, and iteratively, refining haptic effects and evaluating the haptic effects with end users, through such tools as user evaluations involving questionnaires or performance data, which can be a time consuming process.

SUMMARY

One embodiment is a system that automatically adjusts a haptic effect. The system generates a haptic effect based on one or more haptic parameters. The system further measures an affective state of a user that experiences the haptic effect. The system further adjusts at least one haptic parameter of the one or more haptic parameters based on the measured affective state of the user. The system further generates a new haptic effect based on the one or more haptic parameters, where the at least one adjusted haptic parameter causes the new haptic effect to be different from the haptic effect.

BRIEF DESCRIPTION OF THE DRAWINGS

Further embodiments, details, advantages, and modifications will become apparent from the following detailed description of the preferred embodiments, which is to be taken in conjunction with the accompanying drawings.

DETAILED DESCRIPTION

One embodiment is a system that can automatically adjust haptic effects by measuring an affective state of a user that experiences the haptic effects. The measuring can be performed by one or more affective sensors that measure affective data, such as a heart rate of the user, a bio signal of the user, or a facial feature of the user that can indicate an emotional state of the user. The system can analyze the measured affective state and can automatically adjust one or more haptic parameters used to generate the haptic effects. By automatically adjusting the one or more haptic parameters, the system can generate new haptic effects in order to produce a desired affective state from the user. The system can perform the generation of the haptic effects, the measuring of the affective state of the user, the analyzing of the measured affective state, and the automatic adjusting of the one or more haptic parameters continuously, in a closed loop, until the haptic effects produce a desired affective state, or a desired change in affective state. For example, a device, such as a mobile device, touchscreen device, personal computer, or smartphone, can automatically adjust the haptic effects it uses for confirmation, and can also use affective sensors, such as bio-sensors, to determine optimal haptic parameters for a balance between pleasantness and noticeability. As another example, a device manufacturer can adjust haptic effects across a significant number of devices by implementing a central server that automatically adjusts haptic effects for each of the devices.

Figure 1:
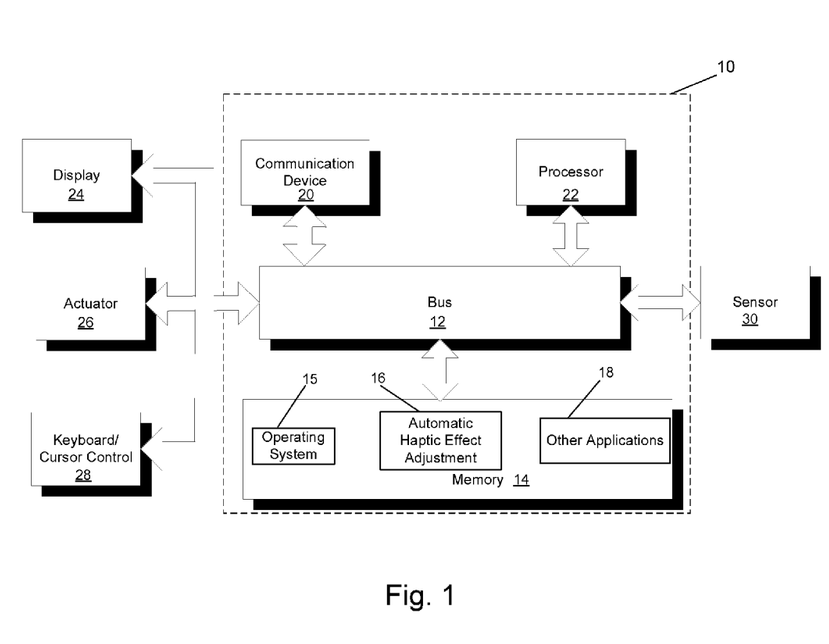
FIG. 1 illustrates a block diagram of a system in accordance with one embodiment of the invention.

FIG. 1 illustrates a block diagram of a system 10 in accordance with one embodiment of the invention. In one embodiment, system 10 is part of a device, and system 10 provides an automatic haptic effect adjustment functionality for the device. In another embodiment, system 10 is separate from the device, and remotely provides the automatic haptic effect adjustment for the device. Although shown as a single system, the functionality of system 10 can be implemented as a distributed system, where one or more components of system 10 are physically separate from, but operatively coupled to, the other components of system 10. System 10 includes a bus 12 or other communication mechanism for communicating information, and a processor 22 coupled to bus 12 for processing information. Processor 22 may be any type of general or specific purpose processor. System 10 further includes a memory 14 for storing information and instructions to be executed by processor 22. Memory 14 can be comprised of any combination of random access memory ("RAM"), read only memory ("ROM"), static storage such as a magnetic or optical disk, or any other type of computer-readable medium.

A computer-readable medium may be any available medium that can be accessed by processor 22 and may include both a volatile and nonvolatile medium, a removable and non-removable medium, a communication medium, and a storage medium. A communication medium may include computer readable instructions, data structures, program modules or other data in a modulated data signal such as a carrier wave or other transport mechanism, and may include any other form of an information delivery medium known in the art. A storage medium may include RAM, flash memory, ROM, erasable programmable read-only memory ("EPROM"), electrically erasable programmable read-only memory ("EEPROM"), registers, hard disk, a removable disk, a compact disk read-only memory ("CD-ROM"), or any other form of a storage medium known in the art.

In one embodiment, memory 14 stores software modules that provide functionality when executed by processor 22. The modules include an operating system 15 that provides operating system functionality for system 10, as well as the rest of a device in one embodiment. The modules further include an automatic haptic effect adjustment module 16 that automatically adjusts a haptic effect, as disclosed in more detail below. In certain embodiments, automatic haptic effect adjustment module 16 can comprise a plurality of modules, where each individual module provides specific individual functionality for automatically adjusting a haptic effect. System 10 will typically include one or more additional application modules 18 to include additional functionality, such as the Integrator™ application by Immersion Corporation.

System 10, in embodiments that transmit and/or receive data from remote sources, further includes a communication device 20, such as a network interface card, to provide mobile wireless network communication, such as infrared, radio, Wi-Fi, or cellular network communication. In other embodiments, communication device 20 provides a wired network connection, such as an Ethernet connection or a modem.

Processor 22 is further coupled via bus 12 to a display 24, such as a Liquid Crystal Display ("LCD"), for displaying a graphical representation or user interface to a user. The display 24 may be a touch-sensitive input device, such as a touchscreen, configured to send and receive signals from processor 22, and may be a multi-touch touchscreen. Processor 22 may be further coupled to a keyboard or cursor control 28 that allows a user to interact with system 10, such as a mouse or a stylus.

System 10, in one embodiment, further includes an actuator 26. Processor 22 may transmit a haptic signal associated with a generated haptic effect to actuator 26, which in turn outputs haptic effects such as vibrotactile haptic effects, electrostatic friction haptic effects, or deformation haptic effects. Actuator 26 includes an actuator drive circuit. Actuator 26 may be, for example, an electric motor, an electro-magnetic actuator, a voice coil, a shape memory alloy, an electro-active polymer, a solenoid, an eccentric rotating mass motor ("ERM"), a linear resonant actuator ("LRA"), a piezoelectric actuator, a high bandwidth actuator, an electroactive polymer ("EAP") actuator, an electrostatic friction display, or an ultrasonic vibration generator. In alternate embodiments, system 10 can include one or more additional actuators, in addition to actuator 26 (not illustrated in FIG. 1). Actuator 26 is an example of a haptic output device, where a haptic output device is a device configured to output haptic effects, such as vibrotactile haptic effects, electrostatic friction haptic effects, or deformation haptic effects, in response to a drive signal. In alternate embodiments, actuator 26 can be replaced by some other type of haptic output device. Further, in other alternate embodiments, system 10 may not include actuator 26, and a separate device from system 10 includes an actuator, or other haptic output device, that generates the haptic effects, and system 10 sends generated haptic effect signals to that device through communication device 20.

System 10, in one embodiment, further includes a sensor 30. Sensor 30 can be configured to detect a form of energy, or other physical property, such as, but not limited to, acceleration, bio signals, distance, flow, force/pressure/strain/bend, humidity, linear position, orientation/inclination, radio frequency, rotary position, rotary velocity, manipulation of a switch, temperature, vibration, or visible light intensity. Sensor 30 can further be configured to convert the detected energy, or other physical property, into an electrical signal, or any signal that represents virtual sensor information. Sensor 30 can be any device, such as, but not limited to, an accelerometer, an electrocardiogram, an electroencephalogram, an electromyograph, an electrooculogram, an electropalatograph, an infrared photoplethysmograph, a pneumograph, a galvanic skin response sensor, a skin conductance meter, a capacitive sensor, a hall effect sensor, an infrared sensor, an ultrasonic sensor, a pressure sensor, a fiber optic sensor, a flexion sensor (or a bend sensor), a force-sensitive resistor, a load cell, a LuSense $CPS^2$ 155, a miniature pressure transducer, a piezo sensor, a strain gage, a hygrometer, a linear position touch sensor, a linear potentiometer (or a slider), a linear variable differential transformer, a compass, an inclinometer, a magnetic tag (or a radio frequency identification tag), a rotary encoder, a rotary potentiometer, a gyroscope, an on-off switch, a temperature sensor (such as a thermometer, a thermocouple, a resistance temperature detector, a thermistor, or a temperature-transducing integrated circuit), a microphone, a camera, an eye tracker, a photometer, an altimeter, a bio monitor, a light-dependent resistor, a text analyzer, or a pattern analyzer.

In alternate embodiments, system 10 can include one or more additional sensors, in addition to sensor 30 (not illustrated in FIG. 1). In some of these alternate embodiments, at least one of the additional sensors can be a context sensor that can be configured to detect context data. One example of context data is data that identifies one or more physical properties of a device. Another example of context data is data that identifies a functionality of a device. Yet another example of context data is data that identifies an interaction with a device. A further example of context data is data that identifies one or more characteristics associated with an interaction with a device, such as pressure, acceleration, sound, or data created by the interaction with the device. Yet a further example of context data is data that identifies a state of a user and/or an environment that a user is in. In certain embodiments, a context sensor can be one of the aforementioned devices delineated in the previous paragraph.

Figure 2:
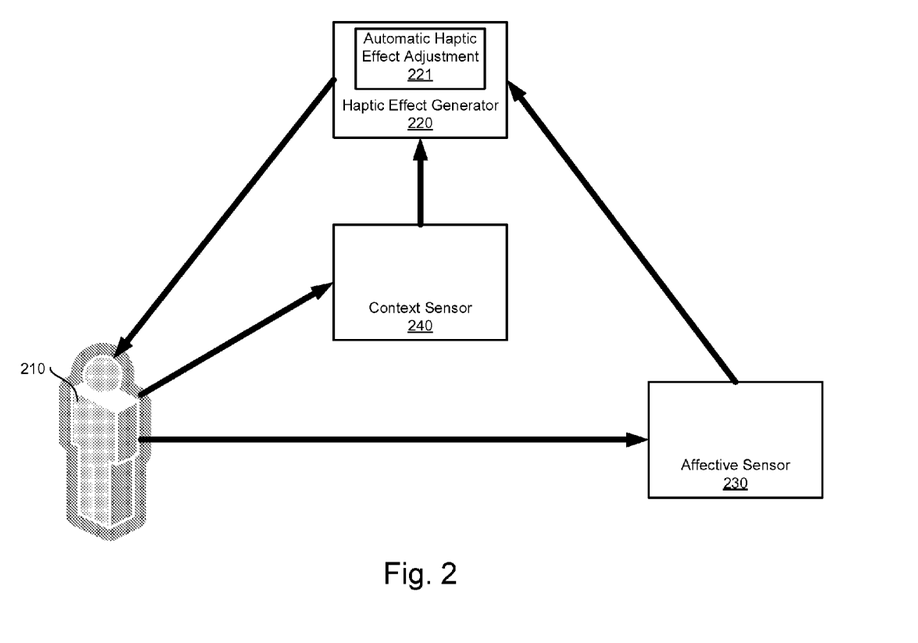
FIG. 2 illustrates a block diagram of an automatic adjustment of a haptic effect, according to one embodiment of the invention.

FIG. 2 illustrates a block diagram of an automatic adjustment of a haptic effect, according to one embodiment of the invention. FIG. 2 includes user 210. User 210 represents a user of a device or system that can generate a haptic effect. As described below in greater detail, user 210 can experience a haptic effect and produce an affective state, or a change in an affective state, as a result of experiencing the haptic effect.

FIG. 2 further includes haptic effect generator 220, which can be implemented by system 10 of FIG. 1. Haptic effect generator 220 includes a hardware component and/or a software component that can generate a haptic effect based on one or more haptic parameters, where the haptic effect can be experienced by user 210. According to the embodiment, haptic effect generator 220 can generate a range of haptic effects that can be experienced by user 210. Examples of haptic effects that can be experienced by user 210 include vibrotactile haptic effects, electrostatic friction haptic effects, or deformation haptic effects. More specifically, in certain embodiments, the software component of haptic effect generator 220 can generate a haptic signal, and send the haptic signal to the hardware component of haptic effect generator 220, where the hardware component can generate the haptic effect based on the haptic signal. In some of these embodiments, the hardware component of haptic effect generator 220 is an actuator. In other embodiments, the software component of haptic effect generator 220 can generate a haptic signal and send the haptic signal to an external device (not illustrated in FIG. 2), where the external device can generate the haptic effect based on the haptic signal. In certain embodiments, haptic effect generator 220 can be distributed across a network, such as between a server, and one or more remote devices operably coupled to the server.

According to the embodiment, a haptic parameter is a parameter that can define a haptic signal used to generate a haptic effect, and thus, can also define the haptic effect to be generated. More specifically, a haptic parameter is a quantity of a haptic effect quality, such as magnitude, frequency, duration, amplitude, strength, envelope, density, or any other kind of quantifiable haptic parameter. According to the embodiment, a haptic effect can be defined, at least in part, by the one or more haptic parameters, where the one or more haptic parameters can define characteristics of the haptic effect. A haptic parameter can include a numeric value, where the numeric value can define a characteristic of the haptic signal, and thus, can also define a characteristic of the haptic effect generated by the haptic signal. Examples of haptic parameters can include: an amplitude haptic parameter, a frequency haptic parameter, a duration haptic parameter, an envelope haptic parameter, a density haptic parameter, a magnitude haptic parameter, and a strength haptic parameter.

According to the embodiment, an amplitude haptic parameter can define an amplitude of a haptic signal used to generate a haptic effect, and thus, can define an amplitude of the haptic effect. A frequency haptic parameter can define a frequency of a haptic signal used to generate a haptic effect, and thus, can define a frequency of the haptic effect. A duration haptic parameter can define a duration of a haptic signal used to generate a haptic effect, and thus, can define a duration of the haptic effect. An envelope haptic parameter can define an envelope of a haptic signal used to generate a haptic effect, and thus, can define an envelope of the haptic effect. A density haptic parameter can define a density of a haptic signal used to generate a haptic effect, and thus, can define a density of the haptic effect. A magnitude haptic parameter can define a magnitude of a haptic signal used to generate a haptic effect, and thus, can define a magnitude of the haptic effect. A strength haptic parameter can define a strength of a haptic signal used to generate a haptic effect, and thus, can define a strength of the haptic effect.

In alternate embodiments, another example of a haptic parameter is an actuator haptic parameter, which can be used to configure a haptic signal to be sent to one or more specified actuators. For example, an actuator haptic parameter can configure a haptic signal to be sent to an LRA actuator, an ERM actuator, or to both actuators. In certain embodiments, an actuator haptic parameter can be associated with a specified actuator. In other embodiment, an actuator haptic parameter can be associated with a plurality of specified actuators.

FIG. 2 further includes automatic haptic effect adjustment module 221, which can be configured to automatically adjust a haptic effect. In certain embodiments, automatic haptic effect adjustment module 221 is identical to automatic haptic effect adjustment module 16 of FIG. 1. More specifically, automatic haptic effect adjustment module 221 can automatically adjust one or more haptic parameters of a haptic effect previously generated by haptic effect generator 220. By automatically adjusting one or more haptic parameters, automatic haptic effect adjustment module 221 can automatically adjust a value of the one or more haptic parameters. As is described below in greater detail, automatic haptic effect adjustment module 221 can automatically adjust the one or more haptic parameters based on input measured from one or more sensors. Such input can include a measured affective state of user 210. Such input can optionally also include a measured context of user 210.

Once automatic haptic effect adjustment module 221 has adjusted the one or more haptic parameters, the software component of haptic effect generator 220 can generate a new haptic signal based on the one or more haptic parameters. In certain embodiments, the software component of haptic effect generator 220 can send the new haptic signal to the hardware component of haptic effect generator 220, where the hardware component can generate a new haptic effect based on the new haptic signal. In other embodiments, the software component of haptic effect generator 220 can send the new haptic signal to an external device (not illustrated in FIG. 2), where the external device can generate the new haptic effect based on the new haptic signal. In the illustrated embodiment, automatic haptic effect adjustment module 221 is a component of haptic effect generator 220. However, in alternate embodiments, automatic haptic effect adjustment module 221 can be separate from haptic effect generator 220.

In one example, haptic effect generator 220 can generate a set of ten original haptic effects. Automatic haptic effect adjustment module 221 can adjust the haptic parameters of each original haptic effect of the set of ten original haptic effects. Automatic haptic effect adjust module 221 can then cause haptic effect generator 220 to generate a set of ten new haptic effects. For each new haptic effect, the one or more adjusted haptic parameters cause the new haptic effect to be different from the original haptic effect.

FIG. 2 further includes affective sensor 230. In certain embodiments, affective sensor 230 is identical to sensor 30 of FIG. 1. Affective sensor 230 can measure an affective state of user 210, where user 210 experiences a haptic effect generated by haptic effect generator 220. More specifically, affective sensor 230 can detect affective data, where affective data includes one or more characteristics of user 210. As an example, affective sensor 230 can be a bio-sensor, and can detect characteristics of user 210, such as heart rate, blood pressure, galvanic skin-response, or muscle contractions. As another example, affective sensor 230 can be a camera or other type of sensor, and can detect characteristics of user 210, such as facial expressions or a gaze direction. As an additional example, affective sensor 230 can be a brain imaging device, and can detect characteristics of user 210, such as electric activity of a brain.

According to the embodiment, affective sensor 230 can detect the affective data and produce an input, such as an electrical signal, or any signal that represents the affective data. Affective sensor 230 can further send the input to automatic haptic effect adjustment module 221, which in the illustrated embodiment of FIG. 2 is a component of haptic effect generator 220. Automatic haptic effect adjustment module 221 can analyze the input sent by affective sensor 230 and can determine an affective state of user 210. An affective state of user 210 represents an emotional state of user 210. Thus, by determining an affective state of user 210 when user 210 experiences a haptic effect, an emotional state of user 210 when experiencing the haptic effect can be estimated. In certain embodiments, an affective state of user 210 can be represented by a valence value and an arousal value. Valence, as used in psychology, especially in connection with an emotional state, is the intrinsic attractiveness (i.e., positive valence) or aversiveness (i.e., negative valence) of an event, objection, or situation. Thus, a positive valence value can represent a positive valence, which can indicate an emotional state such as happiness, contentment, or joy. Further, a negative valence value can represent a negative valence, which can indicate an emotional state such as sadness, anger, or annoyance. Arousal is the state of being aware and reactive to stimuli. A higher arousal value can indicate an emotional state consistent with being engaged and reactive to the stimuli. A lower arousal value can indicate an emotional state consistent with being disengaged and unreactive to the stimuli. Together, a valence value and an arousal value can represent an affective state of user 210.

In certain embodiments, as previously described, affective sensor 230 can detect the affective data and can produce an input, and automatic haptic effect adjustment module 221 can analyze the input sent by affective sensor 230 and can directly determine an affective state of user 210, where the affective state of user 210 can be represented by a valence value and an arousal value. However, in alternate embodiments, an affective state can be measured relative to a baseline. For example, a bio signal may vary from one user to another user. Thus, a comparison to a baseline affective state of that user in a known emotional state may be required in order to determine an absolute affective state. For example, an absolute valence value and an absolute arousal value can be determined by comparing a measured valence value and a measured arousal value to a baseline valence value and a baseline arousal value. Thus, in these alternate embodiments, automatic haptic effect adjustment module 221 can normalize a measured affective state (e.g., a measured valence value and a measured arousal value) based on a baseline affective state (e.g., a baseline valence value and a baseline arousal value) in order to determine an affective state.

According to the embodiment, once automatic haptic effect adjustment module 221 has determined the affective state of user 210, automatic haptic effect adjustment module 221 can compare the measured affective state with a pre-defined affective state. A pre-defined affective state can represent an emotional state of user 210 that is desired, or a change in emotional state that is desired. In other words, it can be desired to generate a haptic effect that causes user 210, when experiencing the haptic effect, to produce a desired emotional state or a desired change in emotional state, where the desired emotional state or desired change in emotional state is represented by the pre-defined affective state. In certain embodiments, a pre-defined affective state can include a pre-defined valence value, and a pre-defined arousal value. By comparing the measured affective state with the pre-defined affective state, automatic haptic effect adjustment module 221 can identify if there is a difference between the measured affective state and the pre-defined affective state. In certain embodiments, the difference between the measured affective state and the pre-defined affective state can include: (1) a difference between a valence value of the measured affective state and a valence value of the pre-defined affective state; (2) a difference between an arousal value of the measured affective state and an arousal value of the pre-defined affective state; or (3) a difference between both the valence value and the arousal value of the measured affective state and the valence value and the arousal value of the pre-defined affective state. Such a difference can indicate that a haptic effect generated by haptic effect generator 220 did not cause user 210 to produce the desired emotional state.

Where automatic haptic effect adjustment module 221 identifies a difference between the measured affective state and the pre-defined affective state, automatic haptic effect adjustment module 221 can use the identified difference to automatically adjust one or more haptic parameters of a haptic effect previously generated by haptic effect generator 220. More specifically, automatic haptic effect adjustment module 221 can identify an adjustment to one or more haptic parameters that will produce a new haptic effect, where the new haptic effect will produce a new affective state of user 210. Further, automatic haptic effect adjustment module 221 can identify that the new affective state is more similar to the pre-defined affective state. By being "more similar" to the pre-defined affective state, a difference between the new affective state and the pre-defined affective state can be less than a difference between the original affective state and the pre-defined affective state. In certain embodiments, by being "more similar" to the pre-defined affective state: (1) the valence value of the new affective state is more similar to the valence value of the pre-defined affective state; (2) the arousal value of the new affective state is more similar to the arousal value of the pre-defined affective state; or (3) both the valence value and the arousal value of the new affective state are more similar to the valence value and the arousal value of the pre-defined affective state. Subsequently, as previously described, automatic haptic effect adjustment module 221 can cause haptic effect generator 220 to generate a new haptic effect, where the new haptic effect causes user 210 to produce the new affective state. In alternate embodiments, automatic haptic effect adjustment module 221 can identify a random adjustment to one or more haptic parameters. Automatic haptic effect adjustment module 221 can cause haptic effect generator 220 to generate a new haptic effect based on the random adjustment to one or more haptic parameters. The new haptic effect can (but not necessarily) cause user 210 to produce a new affective state.

In certain embodiments, the aforementioned functionality can be performed continuously until haptic effect generator 220 generates a new haptic effect that produces a new affective state of user 210 that is similar to the pre-defined affective state. An affective state can be "similar" to a pre-defined affective state when a difference between the affective state and the pre-defined affective state is less than a pre-defined threshold. In certain embodiments, by being "similar" to the pre-defined affective state: (1) a difference between the valence value of the affective state and the valence value of the pre-defined affective state is less than a pre-defined threshold; (2) a difference between the arousal value of the affective state and the arousal value of the pre-defined affective state is less than a pre-defined threshold; or (3) both the difference between the valence value of the affective state and the valence value of the pre-defined affective state, and the difference between the arousal value of the affective state and the arousal value of the pre-defined affective state, are less than a pre-defined threshold.

FIG. 2 further includes context sensor 240. In certain embodiments, context sensor 240 is identical to sensor 30 of FIG. 1. Context sensor 240 is an optional sensor that can measure a context of user 210, where user 210 experiences a haptic effect generated by haptic effect generator 220. More specifically, context sensor 240 is a sensor that can detect context data, where context data includes data that identifies one or more physical properties of a device, data that identifies a functionality of a device, data that identifies an interaction with a device, or data that identifies one or more characteristics associated with an interaction with a device, such as pressure, acceleration, sound, or data created by the interaction with the device. An example of a sensor that can detect context data can be an affective sensor, similar to affective sensor 230. Other examples of sensors that can detect context data can include cameras, microphones, accelerometers, and software agents.

According to the embodiment, context sensor 240 can detect the context data and produce an input, such as an electrical signal, or any signal that represents the context data. Context sensor 240 can further send the input to automatic haptic effect adjustment module 221, which in the illustrated embodiment of FIG. 2 is a component of haptic effect generator 220. Automatic haptic effect adjustment module 221 can analyze the input sent by context sensor 240 and can determine a context of user 210. A context can represent an action (such as an interaction with a device) that user 210 performs at a time that user 210 experiences a haptic effect generated by haptic effect generator 220 and produces an affective state measured by affective sensor 230.

Automatic haptic effect adjustment module 221 can then use the context of user 210, in conjunction with the measured affective state of user 210, to automatically adjust one or more haptic parameters of a haptic effect previously generated by haptic effect generator 220. For example, it can be assumed that a haptic effect may be perceived differently by user 210 based on a context of user 210. In this example, a haptic effect may be perceived differently by user 210 when user 210 is in a noisy environment, such as being in a room crowded with people, as compared to when user 210 is sleeping. More specifically, a user 210 may produce an affective state with a higher valence value when experiencing a loud haptic effect in a noisy environment (e.g., user 210 appreciates the increased volume of the haptic effect, as user 210 may not perceive the haptic effect at a decreased volume). In contrast, a user 210 may produce an affective state with a lower valence value when experiencing a loud haptic effect while user 210 is sleeping (e.g., user 210 is annoyed because the haptic effect has disturbed his sleep). Thus, automatic haptic effect adjustment module 221 can take into account a context of user 210, in combination with an affective state of user 210, in determining how to adjust one or more haptic parameters of a haptic effect previously generated by haptic effect generator 220. In certain embodiments, context sensor 240, and the associated functionality, can be omitted.

Figure 3:
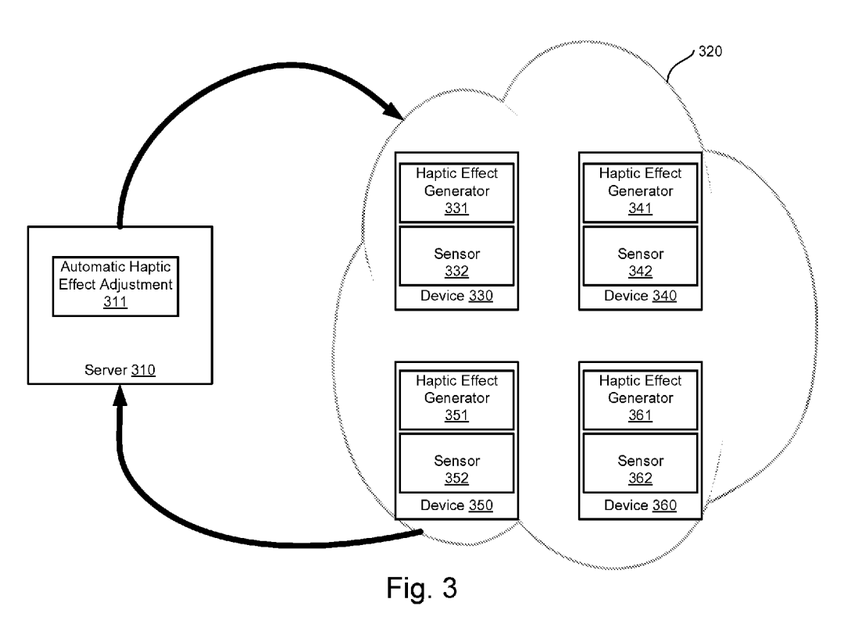
FIG. 3 illustrates a block diagram of a large scale deployment environment, according to one embodiment of the invention.

FIG. 3 illustrates a block diagram of a large scale deployment environment, according to one embodiment of the invention. FIG. 3 includes server 310. Server 310 is a physical device, such as a computer, that can include a memory which stores one or more modules that provides functionality, and that can also include a processor which executes the one or more modules stored within the memory. In the illustrated embodiment of FIG. 3, server 310 also includes automatic haptic effect adjustment module 311, which can be configured to automatically adjust a haptic effect. In certain embodiments, automatic haptic effect adjustment module 311 is identical to automatic haptic effect adjustment module 16 of FIG. 1, and automatic haptic effect adjustment module 221 of FIG. 2.

FIG. 3 further includes network 320. Network 320 is a collection of a plurality of devices, such as mobile devices, touchscreen devices, personal computers, or smartphones, which are operatively interconnected by communication channels that facilitation communication and data transfer among the devices. In certain embodiments, network 320 can be an intranet. In alternate embodiments, network 320 can be the Internet, where the Internet is a global system of interconnected networks that use the standard Internet Protocol suite (i.e., TCP/IP), as understood by one of ordinary skill in the relevant art.

FIG. 3 further includes devices 330, 340, 350 and 360. Devices 330, 340, 350, and 360 are examples of devices that can generate a haptic effect, and that can be operatively coupled to network 320. For example, devices 330, 340, 350, and 360 can be one of, a mobile device, a touchscreen device, a personal computer, or a smartphone. While in the illustrated embodiment, network 320 includes four devices, this is merely an example embodiment, and in other alternate embodiments, network 320 can include any number of devices.

According to the embodiment, device 330 includes haptic effect generator 331 and sensor 332, device 340 includes haptic effect generator 341 and sensor 342, device 350 includes haptic effect generator 351 and sensor 352, and device 360 includes haptic effect generator 361 and sensor 362. Haptic effect generators 331, 341, 351, and 361 each include a hardware component and/or a software component that can generate a haptic effect based on one or more haptic parameters. In certain embodiments, haptic effect generators 331, 341, 351, and 361 are each identical to haptic effect generator 220 of FIG. 2. However, in some of these embodiments, haptic effect generators 331, 341, 351, and 361 do not include an automatic haptic effect adjustment module. In alternate embodiments, at least one of devices 330, 340, 350, and 360 can include additional haptic effect generators not illustrated in FIG. 3.

Further, sensors 332, 342, 352, and 362 can each be configured to measure an affective state of a user, where the user experiences a haptic effect. In certain embodiments, sensors 332, 342, 352, and 362 are each identical to affective sensor 230 of FIG. 2. In alternate embodiments, at least one of devices 330, 340, 350, and 360 can include additional sensors not illustrated in FIG. 3. In some of these embodiments, at least one of the additional sensors can be a sensor that can measure a context of a user, where the user experiences a haptic effect. In these embodiments, the at least one additional sensor can be identical to context sensor 240 of FIG. 2.

According to the embodiment, device 330 generates a haptic effect using haptic effect generator 331, and device 330 measures an affective state of a user that experiences the haptic effect using sensor 332. Similarly, device 340 generates a haptic effect using haptic effect generator 341 and measures an affective state of a user that experiences the haptic effect using sensor 342, device 350 generates a haptic effect using haptic effect generator 351 and measures an affective state of a user that experiences the haptic effect using sensor 352, and device 360 generates a haptic effect using haptic effect generator 361 and measures an affective state of a user that experiences the haptic effect using sensor 362. Further, devices 330, 340, 350, and 360 each send their respective measured affective state to server 310. In certain embodiments, at least one device of devices 330, 340, 350, and 360 can also measure a context of a user that experiences the haptic effect. In these embodiments, the at least one device of devices 330, 340, 350, and 360 can also send the measured context to server 310.

Upon receiving the measured affective states from devices 330, 340, 350, and 360, in accordance with the embodiment, server 310 adjusts one or more haptic parameters based on the measured affective states using automatic haptic effect adjustment module 311. In certain embodiments, server 310 adjusts a single set of one or more haptic parameters collectively for devices 330, 340, 350, and 360. In other embodiments, server 310 adjusts a separate set of one or more haptic parameters individually for each device of devices 330, 340, 350, and 360. Server 310 subsequently sends the one or more haptic parameters to devices 330, 340, 350, and 360. In certain embodiments, server sends the single set of one or more haptic parameters to devices 330, 340, 350, and 360. In other embodiments, server 310 separately sends a first set of one or more haptic parameters to device 330, a second set of one or more haptic parameters to device 340, a third set of one or more haptic parameters to device 350, and a fourth set of one or more haptic parameters to device 360. According to the embodiment, device 330 generates a new haptic effect based on the received one or more haptic parameters using haptic effect generator 331. Similarly, device 340 generates a new haptic effect based on the received one or more haptic parameters using haptic effect generator 341, device 350 generates a new haptic effect based on the received one or more haptic parameters using haptic effect generator 351, and device 360 generates a new haptic effect based on the received one or more haptic parameters using haptic effect generator 361.

Thus, in one example, a device manufacturer or service provider can optimize a set of one or more haptic effects by testing variations across an entire user base, or across a subset of the user base. As an example, a device manufacturer can randomly select a haptic theme used to create one or more haptic effects, where the haptic theme is preloaded on each device as the device is sold to customers. The devices can then measure an affective state that is produced by the haptic effect (e.g., valence, or arousal), as well as optionally measure a context in which the one or more haptic effects are generated (e.g., ambient noise, or current task). The device manufacturer can then collect each measured affective state, and optionally each measured context, through a network, and can store the collected affective state(s), and optionally store the context(s), at a server (such as in a database stored on the server). The device manufacturer can then further analyze the collected affective state(s), and optionally analyze the collected context(s,) and select a new haptic effect that is most likely to lead to a pre-defined affective state in different contexts. New haptic effects can then be sent to the devices. The new haptic effects can be the identified haptic effects that are most likely to lead to a pre-defined affective state, or can be another set of haptic effects used to measure further affective states (and, optionally, further contexts).

Figure 4:
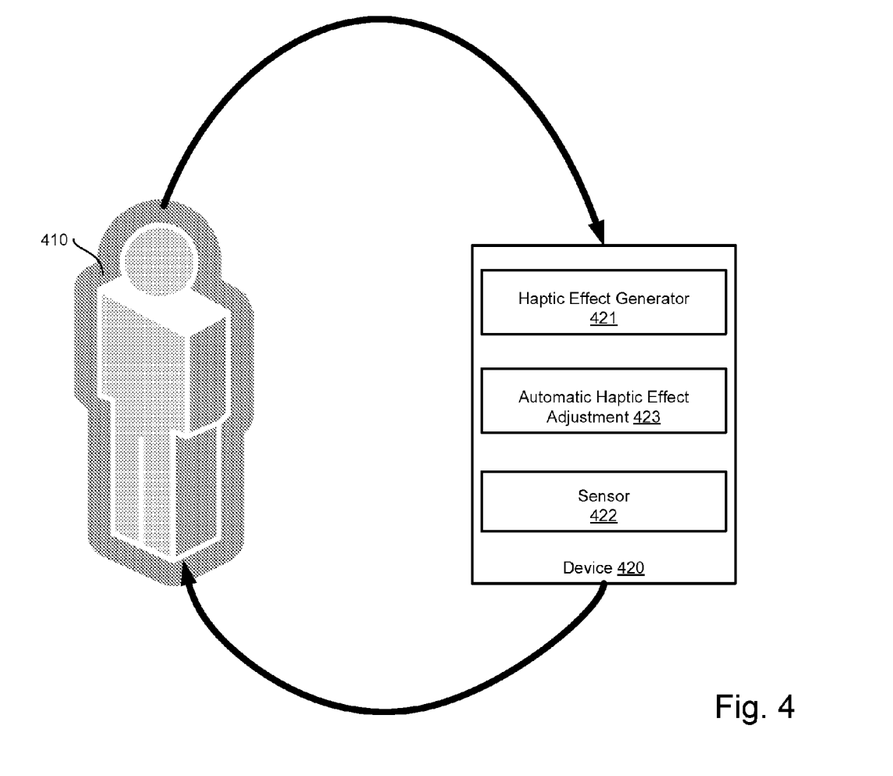
FIG. 4 illustrates a block diagram of an individual deployment environment, according to one embodiment of the invention.

FIG. 4 illustrates a block diagram of an individual deployment environment, according to one embodiment of the invention. FIG. 4 includes user 410. User 410 represents a user of a device or system that can generate a haptic effect. As previously described, user 410 can experience a haptic effect and produce an affective state as a result of experiencing the haptic effect.

FIG. 4 also includes device 420. Device 420 is an example of a device that can generate a haptic effect. For example, device 420 can be one of, a mobile device, a touchscreen device, a personal computer, or a smartphone. According to the embodiment, device 420 includes haptic effect generator 421, sensor 422, and automatic haptic effect adjustment module 423. Haptic effect generator 421 includes a hardware component and/or a software component that can generate a haptic effect based on one or more haptic parameters. In certain embodiments, haptic effect generator 421 is identical to haptic effect generator 220 of FIG. 2, and haptic effect generators 331, 341, 351, and 361 of FIG. 3. However, in some of these embodiments, haptic effect generator 421 does not include an automatic haptic effect adjustment module. In alternate embodiments, device 420 can include additional haptic effect generators not illustrated in FIG. 4.

Sensor 422 can be configured to measure an affective state of a user, where the user experiences a haptic effect. In certain embodiments, sensor 422 is identical to affective sensor 230 of FIG. 2, and sensors 332, 342, 352, and 362 of FIG. 3. In alternate embodiments, device 420 can include additional sensors not illustrated in FIG. 4. In some of these embodiments, at least one of the additional sensors can be a sensor that can measure a context of a user, where the user experiences a haptic effect. In these embodiments, the at least one additional sensor can be identical to context sensor 240 of FIG. 2.

Automatic haptic effect adjustment module 423 can be configured to automatically adjust a haptic effect. In certain embodiments, automatic haptic effect adjustment module 423 is identical to automatic haptic effect adjustment module 16 of FIG. 1, automatic haptic effect adjustment module 221 of FIG. 2, and automatic haptic effect adjustment module 311 of FIG. 3.

According to the embodiment, device 420 generates a haptic effect using haptic effect generator 421, and device 420 measures an affective state of user 410, where user 410 experiences the haptic effect, using sensor 422. Based on the measured affective state of user 410, device 420 adjusts one or more haptic parameters using automatic haptic effect adjustment module 423. Device 420 further generates a new haptic effect based on the one or more haptic parameters using haptic effect generator 421.

In one embodiment, device 420 can further measure a new affective state of user 410, where user 410 experiences the new haptic effect, using sensor 422. Based on the new measured affective state of user 410, device 420 can further adjust one or more haptic parameters using automatic haptic effect adjustment module 423, and can further generate a new haptic effect based on the one or more haptic parameters using haptic effect generator 421. In this embodiment, device 420 can perform the aforementioned functionality continuously until the new haptic effect produces a new affective state of user 410 that is similar to a pre-defined affective state.

Thus, in one example, a device can automatically adjust a set of one or more haptic effects based on an affective state of its user. The device can automatically introduce variations in one or more haptic parameters of the set of one or more haptic effects, such as an intensity of frequency, and can measure an affective state of the user using one or more affective sensors. Thus, the device can gradually learn an optimal set of one or more haptic effects for the specific user, and can adapt to the user's personal preferences. The adjusting can be continuous, thereby adapting to the user's changing preferences over time. Further, the adjustment results can optionally be communicated to a device manufacturer, through a network, to allow the device manufacturer to select a default haptic theme used to generate one or more haptic effects for all of the device manufacturer's devices.

Figure 5:
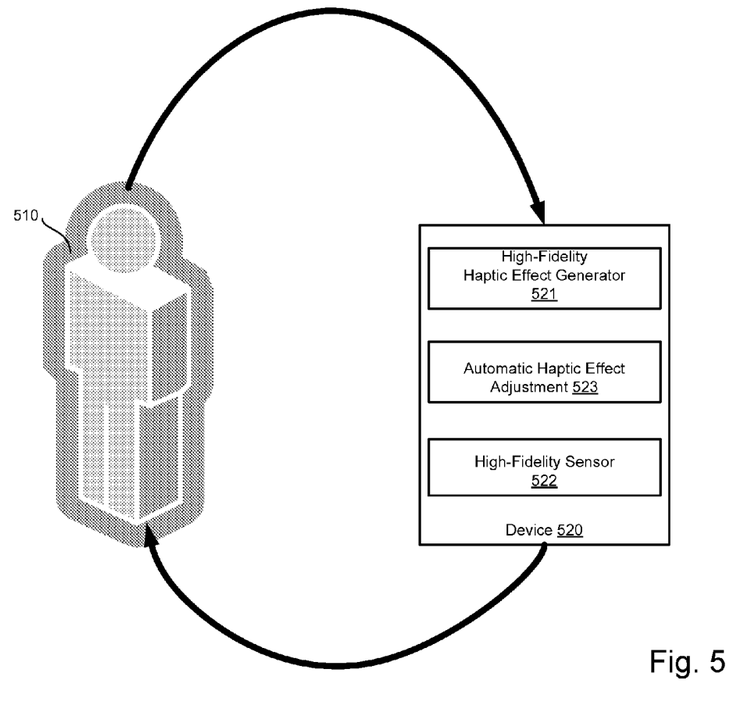
FIG. 5 illustrates a block diagram of a laboratory environment, according to one embodiment of the invention.

FIG. 5 illustrates a block diagram of a laboratory environment, according to one embodiment of the invention. FIG. 5 includes user 510, which is identical to user 410 of FIG. 4, and is not further described here. FIG. 5 further includes device 520, which includes high-fidelity haptic effect generator 521, high-fidelity sensor 522, and automatic haptic effect adjustment module 523. Automatic haptic effect adjustment module 523 is identical to automatic haptic effect adjustment 423 of FIG. 4, and is also not further described here.

High-fidelity haptic effect generator 521 includes a hardware component and/or a software component that can generate a haptic effect based on one or more haptic parameters. In this embodiment, the hardware component of high-fidelity haptic effect generator 521 is a high-fidelity actuator. According to the embodiment, a high-fidelity actuator is an actuator configured to only generate a haptic effect of a pre-defined resolution or higher. In alternate embodiments, device 520 can include additional high-fidelity haptic effect generators not illustrated in FIG. 5. In other alternate embodiments, high-fidelity haptic effect generator 521 can be replaced by a haptic effect generator (such as haptic effect generator 421 of FIG. 4).

High-fidelity sensor 522 is configured to measure an affective state of a user, where the user experiences a haptic effect. According to the embodiment, high-fidelity sensor 522 only measures the affective state using a pre-defined resolution or higher. In certain embodiments, high-fidelity sensor 522 is a high-fidelity affective sensor 522. In alternate embodiments, device 520 can include additional high-fidelity sensors not illustrated in FIG. 5. In some of these embodiments, at least one of the additional sensors can be a high-fidelity sensor that can measure a context of a user, where the user experiences a haptic effect. In these embodiments, the at least one additional high-fidelity sensor can be a high-fidelity context sensor. According to the embodiment, a fidelity context sensor only measures the context using a pre-defined resolution or higher.

According to the embodiment, device 520 generates a haptic effect using high-fidelity haptic effect generator 521, and device 520 measures an affective state of user 510, where user 510 experiences the haptic effect, using high-fidelity sensor 522. Based on the measured affective state of user 510, device 520 adjusts one or more haptic parameters using automatic haptic effect adjustment module 523. Device 520 further generates a new haptic effect based on the one or more haptic parameters using high-fidelity haptic effect generator 521.

In one embodiment, device 520 can further measure a new affective state of user 510, where user 510 experiences the new haptic effect, using high-fidelity sensor 522. Based on the new measured affective state of user 510, device 520 can further adjust one or more haptic parameters using automatic haptic effect adjustment module 523, and can further generate a new haptic effect based on the one or more haptic parameters using high-fidelity haptic effect generator 521. In this embodiment, device 520 can perform the aforementioned functionality continuously until the new haptic effect produces a new affective state of user 510 that is similar to a pre-defined affective state.

Thus, in one example, haptic effects can be automatically adjusted in an experimental environment rather than an environment that includes deployed devices. In this example, a user can use a device that generates a set of one or more haptic effects using high-fidelity haptic generators, and that measures an affective state with one or more high-fidelity sensors, such as brain imaging devices. A set of one or more haptic effects can be tried iteratively, with each iteration being directed by the measured affective states. This can be particularly valuable in a marketing scenario. For example, an affective state produced as a result of an online advertisement's haptic effects can be adjusted to produce a pre-defined affective state.

Figure 6:
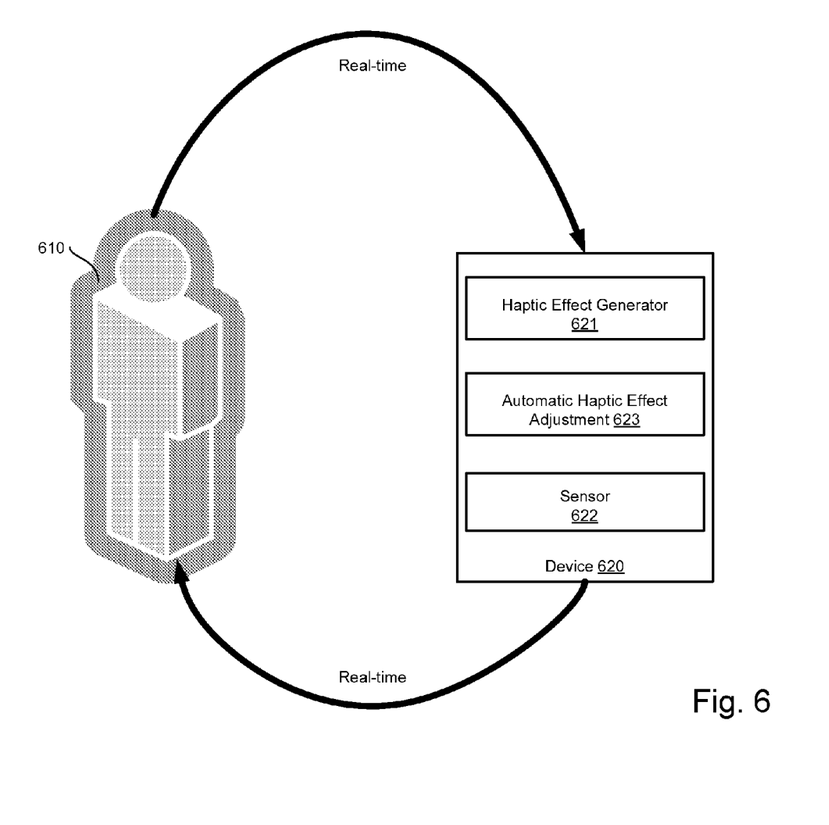
FIG. 6 illustrates a block diagram of an individual deployment environment including real-time continuous adjustment of a haptic effect, according to one embodiment of the invention.

FIG. 6 illustrates a block diagram of an individual deployment environment including real-time continuous adjustment of a haptic effect, according to one embodiment of the invention. FIG. 6 includes user 610, which is identical to user 410 of FIG. 4, and is not further described here. FIG. 6 further includes device 620, which includes haptic effect generator 621, sensor 622, and automatic haptic effect adjustment module 623. Haptic effect generator 621 is identical to haptic effect generator 421 of FIG. 4, sensor 622 is identical to sensor 422 of FIG. 4, and automatic haptic effect adjustment module 623 is identical to automatic haptic effect adjustment 423. Thus, haptic effect generator 621, sensor 622, and haptic effect adjustment module 623 are also not further described here.

According to the embodiment, device 620 generates a haptic effect using haptic effect generator 621, and device 620 measures an affective state of user 610, where user 610 experiences the haptic effect, using sensor 622. Based on the measured affective state of user 610, device 620 adjusts one or more haptic parameters using automatic haptic effect adjustment module 623. Device 620 further generates a new haptic effect based on the one or more haptic parameters using haptic effect generator 621. In this embodiment, device 620 performs the aforementioned functionality in real-time. As understood by one of ordinary skill in the art, "real-time" means occurring immediately or substantially immediately (e.g., within five milliseconds).

In one embodiment, device 620 can further measure a new affective state of user 610, where user 610 experiences the new haptic effect, using sensor 622. Based on the new measured affective state of user 610, device 620 can further adjust one or more haptic parameters using automatic haptic effect adjustment module 623, and can further generate a new haptic effect based on the one or more haptic parameters using haptic effect generator 621. In this embodiment, device 620 can perform the aforementioned functionality continuously, and in real-time, until the new haptic effect produces a new affective state of user 610 that is similar to a pre-defined affective state.

Thus, in one example, haptic effects can be adjusted continuously, in real-time, until a desired affective state or a desired change in affective state is produced, as measured by one or more sensors. For example, a notification haptic effect can gradually increase in intensity until one or more affective sensors indicate that the haptic effect has been noticed by the user. Similarly, an intensity of a continuous haptic effect can be reduced until it is determined that the haptic effect is no longer unpleasant for the user, based on the measured affective state of the user.

Figure 7:
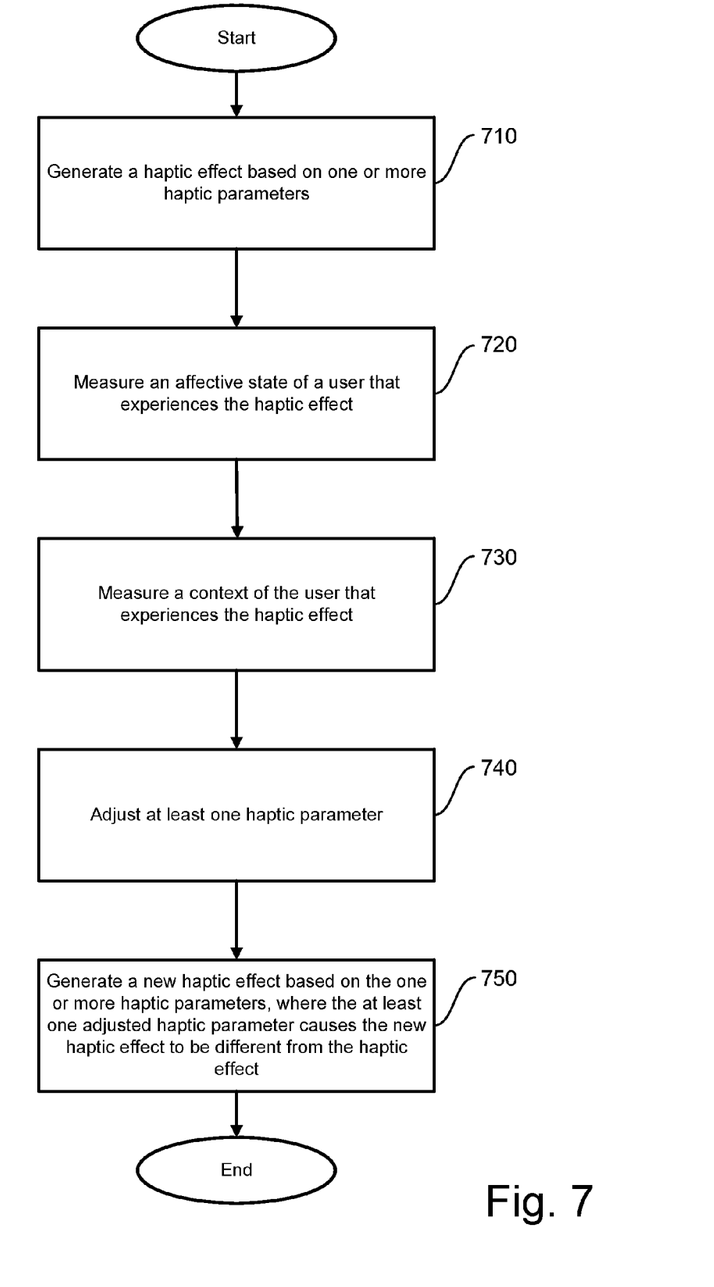
FIG. 7 illustrates a flow diagram of the functionality of an automatic haptic effect adjustment module, according to one embodiment of the invention.

FIG. 7 illustrates a flow diagram of the functionality of an automatic haptic effect adjustment module (such as automatic haptic effect adjustment module 16 of FIG. 1), according to one embodiment of the invention. In one embodiment, the functionality of FIG. 7 is implemented by software stored in memory or another computer-readable or tangible medium, and executed by a processor. In other embodiments, the functionality may be performed by hardware (e.g., through the use of an application specific integrated circuit ("ASIC"), a programmable gate array ("PGA"), a field programmable gate array ("FPGA"), etc.), or any combination of hardware and software. Furthermore, in alternate embodiments, the functionality may be performed by hardware using analog components.

The flow begins and proceeds to 710. At 710, a haptic effect is generated that is based on one or more haptic parameters. In certain embodiments, the one or more haptic parameters include at least one of: an amplitude haptic parameter, a frequency haptic parameter, a duration haptic parameter, an envelope haptic parameter, a density haptic parameter, a magnitude haptic parameter, a strength haptic parameter, or an actuator haptic parameter. In certain embodiments, the haptic effect is generated as follows. A haptic signal is generated based on the one or more haptic parameters. The haptic signal is subsequently sent to an actuator to generate the haptic effect. The flow proceeds to 720.

At 720, an affective state of a user that experiences the haptic effect is measured. In certain embodiments, an affective state of the user can include a valence value and an arousal value. A valance value can indicate either a positive valence or a negative valence associated with the haptic effect. An arousal value can indicate a state of awareness of the haptic effect. In certain embodiments, the affective state is measured as follows. An input produced by an affective sensor configured to detect affective data is measured. Affective data can include one or more characteristics of the user. The input is subsequently analyzed to determine the affective state of the user. The flow proceeds to 730.

At 730, a context of the user that experiences the haptic effect is measured. In certain embodiment, a context of the user can represent an action (such as an interaction with a device) that the user performs at a time that the user experiences a haptic effect. In certain embodiments, the context is measured as follows. An input produced by a context sensor configured to detect context data can be measured. Context data can include one or more physical properties of a device, data that identifies a functionality of a device, data that identifies an interaction with a device, or one or more characteristics associated with an interaction with a device, such as pressure, acceleration, sound, or data created by the interaction with the device. The input is subsequently analyzed to determine the context of the user. In certain embodiments, 730 can be omitted. The flow proceeds to 740.

At 740, at least one haptic parameter of the one or more haptic parameters is adjusted based on the measured affective state of the user. In certain embodiments, the at least one haptic parameter is adjusted as follows. A difference between a measured affective state and a pre-defined affective state is identified. At least one value of the at least one haptic parameter is subsequently adjusted in order to reduce the identified difference. In certain embodiments where the context of the user is also measured, the at least one haptic parameter can be adjusted based also on the measured context of the user. The flow proceeds to 750.

At 750, a new haptic effect is generated based on the one or more haptic parameters, where the at least one adjusted haptic parameter causes the new haptic effect to be different from the haptic effect. The new haptic effect can produce a new affective state of the user, where the new affective state is more similar to the pre-defined affective state. In certain embodiments, the new haptic effect is generated as follows. A new haptic signal is generated based on the one or more haptic parameters that include the at least one adjusted haptic parameter. The new haptic signal is subsequently sent to the actuator to generate the new haptic effect. The flow then ends.

In certain embodiments, the generating of the haptic effect at 710, the measuring of the affective state at 720, the measuring of the context at 730, and the generating of the new haptic effect at 750 are each performed at a device. In these embodiments, the adjusting of the at least one haptic parameter at 740 is performed at a server. Also, in these embodiments, the device sends the measured affective state and measured context to the server, and the server sends the one or more haptic parameters to the device. In some of these embodiments, the server automatically adjusts a haptic effect for a plurality of devices.

In alternate embodiments, the generating of the haptic effect at 710, the measuring of the affective state at 720, the measuring of the context at 730, the adjusting of the at least one haptic parameter at 740, and the generating of the new haptic effect at 750 are each performed at a device. In some of these embodiments, the generating of the haptic effect at 710, the measuring of the affective state at 720, the measuring of the context at 730, the adjusting of the at least one haptic parameter at 740, and the generating of the new haptic effect at 750 are performed continuously until the new haptic effect produces a new affective state of the user that is similar to a pre-defined affective state. Further, in some of these embodiments, the generating of the haptic effect at 710, the measuring of the affective state at 720, the measuring of the context at 730, the adjusting of the at least one haptic parameter at 740, and the generating of the new haptic effect at 750 are performed in real-time. Further, in some of these embodiments, the generating of the haptic effect at 710 is performed by a high-fidelity actuator. Finally, in some of these embodiments, the measuring of the affective state at 720 is performed by a high-fidelity affective sensor.

Thus, according to an embodiment, a system is provided that can generate a haptic effect, measure an affective state of a user that experiences the haptic effect, and automatically adjust the haptic effect based on the affective state. The system can optionally measure a context of the user that experiences the haptic effect, and further automatically adjust the haptic effect based on the context. By closing a loop between generating a haptic effect and measuring an affective state of a user that experiences the haptic effect (and optionally a context of the user that experiences the haptic effect), the system can reduce the time required to adjust haptic effects, and increase the amount of data available for adjusting haptic effects. The system can further increase the realism and variety of testing conditions for measuring an affective state of a user, and can allow personalization of haptic effects, and adjustments of haptic effects, over time.

The features, structures, or characteristics of the invention described throughout this specification may be combined in any suitable manner in one or more embodiments. For example, the usage of "one embodiment," "some embodiments," "certain embodiment," "certain embodiments," or other similar language, throughout this specification refers to the fact that a particular feature, structure, or characteristic described in connection with the embodiment may be included in at least one embodiment of the present invention. Thus, appearances of the phrases "one embodiment," "some embodiments," "a certain embodiment," "certain embodiments," or other similar language, throughout this specification do not necessarily all refer to the same group of embodiments, and the described features, structures, or characteristics may be combined in any suitable manner in one or more embodiments.

One having ordinary skill in the art will readily understand that the invention as discussed above may be practiced with steps in a different order, and/or with elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

I claim:

1. A non-transitory computer-readable medium having instructions stored thereon that, when executed by a processor, cause the processor to automatically adjust a haptic effect, the automatic adjusting comprising:

generating a haptic effect based on one or more haptic parameters;

measuring an affective state of a user that experiences the haptic effect;

measuring a context of the user that experiences the haptic effect;

adjusting at least one haptic parameter of the one or more haptic parameters based on the measured affective state of the user and the measured context of the user; and generating a new haptic effect based on the one or more haptic parameters, wherein the at least one adjusted haptic parameter causes the new haptic effect to be different from the haptic effect.

2. The non-transitory computer-readable medium of claim 1, wherein the measuring the affective state further comprises:
measuring an input produced by an affective sensor configured to detect affective data, wherein the affective data comprises one or more characteristics of the user; and
analyzing the input to determine the affective state of the user.

3. The non-transitory computer-readable medium of claim 2, wherein the affective state comprises a valence value and an arousal value.

4. The non-transitory computer-readable medium of claim 1, wherein the adjusting the at least one haptic parameter further comprises:
identifying a difference between the measured affective state and a pre-defined affective state; and
adjusting at least one value of the at least one haptic parameter to reduce the identified difference.

5. The non-transitory computer-readable medium of claim 4,
wherein the new haptic effect produces a new affective state of the user; and
wherein the new affective state is more similar to the pre-defined affective state.

6. The non-transitory computer-readable medium of claim 1, wherein the one or more haptic parameters comprises at least one of: an amplitude haptic parameter, a frequency haptic parameter, a duration haptic parameter, an envelope haptic parameter, a density haptic parameter, a magnitude haptic parameter, a strength haptic parameter, or an actuator haptic parameter.

7. The non-transitory computer-readable medium of claim 1,
wherein the adjusting the at least one haptic parameter is performed at a server;
wherein the generating the haptic effect, the measuring the affective state, and the generating the new haptic effect are performed at a device;
wherein the device sends the measured affective state to the server; and
wherein the server sends the one or more haptic parameters to the device.

8. The non-transitory computer-readable medium of claim 7, wherein the server automatically adjusts a haptic effect for a plurality of devices.

9. The non-transitory computer-readable medium of claim 1, wherein the generating the haptic effect, the measuring the affective state, the adjusting the at least one haptic parameter, and the generating the new haptic effect are performed at a device.

10. The non-transitory computer-readable medium of claim 9, wherein the measuring the affective state, the adjusting the at least one haptic parameter, and the generating the new haptic effect are performed continuously until the new haptic effect produces a new affective state of the user that is similar to a pre-defined affective state.

11. The non-transitory computer-readable medium of claim 10 wherein the measuring the affective state, the adjusting the at least one haptic parameter, and the generating the new haptic effect are performed in real-time.

12. The non-transitory computer-readable medium of claim 9,
wherein the measuring the affective state further comprises measuring an input produced by a high-fidelity affective sensor that detects one or more characteristics of the user.

13. The non-transitory computer-readable medium of claim 12,
wherein the generating the haptic effect further comprises sending a generated haptic signal to a high-fidelity actuator to generate the haptic effect.

14. The non-transitory computer-readable medium of claim 1, wherein the generating the haptic effect further comprises:
generating a haptic signal based on the one or more haptic parameters; and
sending the haptic signal to an actuator to generate the haptic effect.

15. The non-transitory computer-readable medium of claim 14, wherein the generating the new haptic effect further comprises:
generating a new haptic signal based on the one or more haptic parameters comprising the at least one adjusted haptic parameter; and
sending the new haptic signal to the actuator to generate the new haptic effect.

16. A computer-implemented method for automatically adjusting a haptic effect, the computer-implemented method comprising:
generating a haptic effect based on one or more haptic parameters;
measuring an affective state of a user that experiences the haptic effect;
measuring a context of the user that experiences the haptic effect;
adjusting at least one haptic parameter of the one or more haptic parameters based on the measured affective state of the user and the measured context of the user; and
generating a new haptic effect based on the one or more haptic parameters, wherein the at least one adjusted haptic parameter causes the new haptic effect to be different from the haptic effect.

17. The computer-implemented method of claim 16, wherein the measuring the affective state further comprises:
measuring an input produced by an affective sensor configured to detect affective data, wherein the affective data comprises one or more characteristics of the user; and
analyzing the input to determine the affective state of the user.

18. The computer-implemented method of claim 17, wherein the affective state comprises a valence value and an arousal value.

19. The computer-implemented method of claim 16, wherein the adjusting the at least one haptic parameter further comprises:
identifying a difference between the measured affective state and a pre-defined affective state; and
adjusting a value of the at least one haptic parameter based on the identified difference.

20. A system for automatically adjusting a haptic effect, the system comprising:
a memory configured to store an automatic haptic effect adjustment module; and
a processor configured to execute the automatic haptic effect adjustment module stored on the memory;

wherein the automatic haptic effect adjustment module is configured to generate a haptic effect based on one or more haptic parameters;

wherein the automatic haptic effect adjustment module is further configured to measure an affective state of a user that experiences the haptic effect;

wherein the automatic haptic effect adjustment module is further configured to measure a context of the user that experiences the haptic effect;

wherein the automatic haptic effect adjustment module is further configured to adjust at least one haptic parameter of the one or more haptic parameters based on the measured affective state of the user and based on the measured context of the user;

wherein the automatic haptic effect adjustment module is further configured to generate a new haptic effect based on the one or more haptic parameters; and wherein the at least one adjusted haptic parameter causes the new haptic effect to be different from the haptic effect.

21. The system of claim 20, wherein the automatic haptic effect adjustment module is further configured to measure an input produced by an affective sensor configured to detect affective data, wherein the affective data comprises one or more characteristics of the user; and wherein the automatic haptic effect adjustment module is further configured to analyze the input to determine the affective state of the user.

22. The system of claim 20, wherein the automatic haptic effect adjustment module is further configured to identify a difference between the measured affective state and a pre-defined affective state; and wherein the automatic haptic effect adjustment module is further configured to adjust a value of the at least one haptic parameter based on the identified difference.

* * * * *